United States Patent
Hoernig

(10) Patent No.: US 11,830,612 B2
(45) Date of Patent: Nov. 28, 2023

(54) CONTROL UNIT AND CONTROL METHOD FOR CONTROLLING AN OUTPUT UNIT FROM INFORMATION IN THE CONTEXT OF MEDICAL DIAGNOSTICS AND THERAPY

(71) Applicant: Siemens Healthcare GmbH, Erlangen (DE)

(72) Inventor: Mathias Hoernig, Moehrendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 901 days.

(21) Appl. No.: 16/532,667

(22) Filed: Aug. 6, 2019

(65) Prior Publication Data
US 2020/0051689 A1     Feb. 13, 2020

(30) Foreign Application Priority Data

Aug. 13, 2018  (EP) ..................................... 18188666

(51) Int. Cl.
*G16H 40/60*     (2018.01)
*G10L 15/22*     (2006.01)
(Continued)

(52) U.S. Cl.
CPC ............. *G16H 40/60* (2018.01); *G10L 15/22* (2013.01); *G10L 17/00* (2013.01); *G16H 40/20* (2018.01); *A61B 34/25* (2016.02); *A61B 2017/00115* (2013.01); *A61B 2017/00203* (2013.01); *G06Q 10/06316* (2013.01); *G10L 2015/223* (2013.01)

(58) Field of Classification Search
USPC .................................................. 386/200–234
See application file for complete search history.

(56) References Cited

U.S. PATENT DOCUMENTS

2001/0047265 A1* 11/2001 Sepe, Jr. ................. G10L 15/22
                                                                            704/E15.04
2015/0332196 A1    11/2015 Stiller et al.
(Continued)

FOREIGN PATENT DOCUMENTS

EP             2945087 A2      11/2015

OTHER PUBLICATIONS

European Search Report with Application No. 18188666.4 dated Jan. 28, 2019.
Extended European Search Report dated Dec. 10, 2020.

*Primary Examiner* — Hung Q Dang
(74) *Attorney, Agent, or Firm* — Harness, Dickey & Pierce, P.L.C.

(57) ABSTRACT

A method is for creating a controller for controlling an output unit from information in the context of medical diagnostics and therapy. The method includes providing a learning processing apparatus designed via an algorithm to recognize spoken words; providing on, or in, the learning processing apparatus, an untrained controller, designed to be trained via machine learning; providing a number of speech recordings, each including a communication during a medical procedure, wherein the speech recordings concern comparable medical procedures; performing a speech analysis of the speech recordings; and training the untrained controller according to a machine learning principle based upon the speech analysis of the speech recordings.

19 Claims, 3 Drawing Sheets

(51) Int. Cl.
*G10L 17/00* (2013.01)
*G16H 40/20* (2018.01)
*G16H 40/67* (2018.01)
*A61B 34/00* (2016.01)
*A61B 17/00* (2006.01)
*G06Q 10/0631* (2023.01)

(56) References Cited

U.S. PATENT DOCUMENTS

| | | | |
|---|---|---|---|
| 2018/0099407 A1* | 4/2018 | Nakamura | B25J 13/003 |
| 2018/0151177 A1* | 5/2018 | Gemmeke | G10L 15/22 |
| 2018/0168755 A1* | 6/2018 | Cagle | A61B 34/74 |
| 2019/0201140 A1* | 7/2019 | Yates | A61B 34/25 |
| 2019/0279765 A1* | 9/2019 | Giataganas | G09B 23/28 |
| 2019/0378019 A1* | 12/2019 | Scheutz | G06F 40/00 |
| 2019/0380792 A1* | 12/2019 | Poltaretskyi | A61B 5/1122 |

* cited by examiner

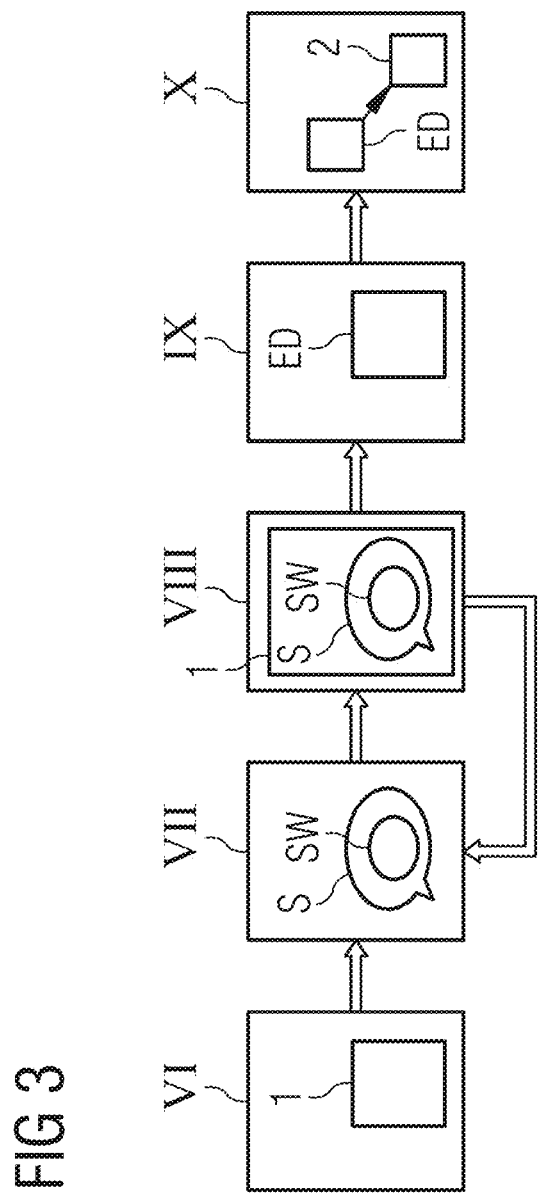

CONTROL UNIT AND CONTROL METHOD FOR CONTROLLING AN OUTPUT UNIT FROM INFORMATION IN THE CONTEXT OF MEDICAL DIAGNOSTICS AND THERAPY

PRIORITY STATEMENT

The present application hereby claims priority under 35 U.S.C. § 119 to European patent application number EP 18188666.4 filed Aug. 13, 2018, the entire contents of which are hereby incorporated herein by reference.

FIELD

Embodiments of the invention generally relate to a control unit and a control method for controlling an output unit from information in the context of medical diagnostics and therapy, and to a method for creating such a control unit and to an information system for the output of information in the context of medical diagnostics and therapy.

BACKGROUND

Clinical workflows and clinical procedures follow medical standards that have been established over many years and are continuously being improved. In particular, these improvements are driven by new, faster, more precise imaging methods, for example 3D methods.

However in the context of improving and automating clinical workflows, for example in surgical interventions, not only the technology used, but also the communication aspect, is very important. For many years now there has been a growing interest in the monitoring and evaluation of this communication in clinical practice.

Beyond purely technical innovations, an accurate understanding of the procedures involved is one problem in the effective optimization and automation of clinical workflows. This includes in particular the communication that has taken place, which is a significant medium for the people present in the examination room (MTAs, physicians, patients). This communication affects the process and duration of the examination, the distribution of tasks, positioning in the examination room, and other aspects.

Initial efforts in this regard were concerned with monitoring one-sided communication from personnel to the patient; later efforts, with general monitoring e.g. for documentation purposes.

In this regard, the extent to which communication in the examination room has changed and varies from procedure to procedure (team to team) is unclear. The extent to which communication can be optimized for a routine is also unclear. Furthermore, it is not known how many commands are necessary, and which ones may be superfluous or even detrimental.

SUMMARY

The inventors have discovered that in current systems and examinations, the language and communication in a clinical workflow is generally not captured and used adequately.

At least one embodiment of the present invention specifies an alternative, more convenient control method and a corresponding control apparatus for controlling an output unit from information in the context of medical diagnostics and therapy, with which the aforementioned disadvantages can be avoided and in particular the communication (amount and type) determined which can improve a workflow.

Embodiments are directed to a method for creating a control unit, a control unit, a control method, and an information system.

At least one embodiment of the present invention is directed to a method serves to create ("train") a control unit that is suitable in particular for controlling an output unit from information in the context of medical diagnostics and therapy. The method comprises:
  providing a learning processing apparatus, wherein the learning processing apparatus is designed via an algorithm to recognize spoken words;
  providing on, or in, the learning processing apparatus, an untrained controller, designed to be trained via machine learning;
  providing a number of speech recordings, each including a communication during a medical procedure, wherein the speech recordings concern comparable medical procedures;
  performing a speech analysis of the speech recordings; and
  training the untrained controller according to a machine learning principle based upon the speech analysis of the speech recordings.

The inventive control unit of at least one embodiment is for controlling an output unit from information in the context of medical diagnostics and therapy is produced using the inventive method. It is a trained control unit that has been trained using embodiments of the inventive method.

At least one embodiment is directed to an inventive controller, for controlling an output unit from information in a context of medical diagnostics and therapy, the controller being configured by at least:
  providing a learning processing apparatus, wherein the learning processing apparatus is designed via an algorithm to recognize spoken words;
  providing on, or in, the learning processing apparatus, an untrained controller, designed to be trained via machine learning;
  providing a number of speech recordings, each including a communication during a medical procedure, wherein the speech recordings concern comparable medical procedures;
  performing a speech analysis of the speech recordings; and
  training the untrained controller according to a machine learning principle based upon the speech analysis of the speech recordings.

The inventive control method of at least one embodiment serves to control in particular an output unit from information in the context of medical diagnostics and therapy. In particular, the control method serves to provide procedure-specific speech capture and analysis in medical diagnostics and therapy in an examination room. It should be noted that statements relating to special characteristics of components of the method described above preferably also apply to the corresponding components of the control method and vice versa. The control method of at least one embodiment includes:
  Providing an inventive (trained) control unit or training a control unit in accordance with a method according to the invention.
  Creating a speech recording during a medical procedure. In one simple case, this can involve the audio from a medical procedure being recorded (e.g. using microphones) during the workflow in an examination room. As a matter of course, the control unit must then have been trained on this procedure. A control unit that has been trained with speech recordings of a hip operation, for example, cannot be used effectively in a cardiac operation.

Processing the speech recording via the control unit while continuing to create the speech recording. This means that the control method is applied during the medical procedure. One part of the communication during the procedure is recorded, processed, and then the next part is recorded and processed.

In this context the control unit determines keywords in the speech recording and generates result output data based on the keywords. Individual keywords or keyword sequences (or combinations of keywords) may be used here. Essentially this principle was preferably also used during the training of the control unit. Here, the determination of keywords was performed by the learning processing apparatus, and the control unit trained to recognize these keywords. Nevertheless, the learning processing apparatus determined the result that followed these keywords and, during the training of the control unit, this result is linked to the respective keyword in the form of result output data.

Controlling the output unit with the result output data.

In this step, the result is preferably output acoustically via speech output, or optically e.g. through text, images or videos. The output may be provided on screens or through loudspeakers as the output unit. The output unit may then be controlled directly (e.g. a loudspeaker in an operating room) or also controlled via the internet.

An inventive information system of at least one embodiment for the output of information in the context of medical diagnostics and therapy comprises an inventive control unit of at least one embodiment, an output unit and a speech recording system, wherein the information system is designed to execute at least one embodiment of the inventive control method.

An inventive learning processing apparatus of at least one embodiment comprises a processor and a data storage device containing instructions which, on being executed, allow the processor to:

capture speech recordings provided to the learning processing apparatus, perform an analysis of the speech recordings (in particular, to recognize spoken words in the speech recordings as objects), if applicable, identify keywords from the words recognized and train a control unit according to at least one embodiment of an inventive method based on the analysis of the speech recordings.

A majority of the aforementioned components of the information system or control unit may be realized entirely or partially in the form of software modules in a processor of a corresponding information system. A realization largely through software has the advantage that conventionally used apparatuses can also easily be upgraded with a software update in order to operate in the manner according to of at least one embodiment the invention.

In this respect, at least one embodiment is also achieved by a corresponding computer program product comprising a computer program, which can be loaded directly into a computing system or a memory device of an information system and which contains program segments, in order to perform all the steps of the method according to of at least one embodiment the invention when the program is executed in the computing system or the information system. Such a computer program product can comprise, where relevant, in addition to the computer program, further components, such as, for example, documentation and/or additional components including hardware components, for example, hardware keys (dongles, etc.) in order to use the software.

For transfer to the computing system or to the information system, and/or for storage on, or in, the computing system or the information system, a computer-readable medium, for instance a memory stick, a hard disk or any other portable or permanently installed data storage medium can be used, on which are stored the program segments of the computer program, which program segments can be downloaded and executed by a computing system or an information system. For this, the processing unit can have, for example, one or more cooperating microprocessors or the like.

Therefore also preferred is an information system in the form of a computer program product comprising a computer program which can be loaded directly into a memory device of the information system and which contains program segments in order to perform all the steps of the identification method according to of at least one embodiment the invention when the computer program is executed in the information system.

An information system or an embodiment of the method or control method is preferred in the form of a computer-readable medium, on which are stored program segments which can be downloaded and executed by a processing unit in order to perform all the steps of a method or control method according to of at least one embodiment the invention when the program segments are executed by the processing unit. The identification unit in the form of this computer-readable medium can also exist as hardware, for instance as a programmed FPGA or EPROM.

BRIEF DESCRIPTION OF THE DRAWINGS

The invention is described again below in greater detail using example embodiments and with reference to the accompanying figures. In the various figures, the same components are identified with identical reference signs. The figures are in general not to scale. In the drawings:

FIG. 3 shows a flow diagram for a possible workflow of an embodiment of an inventive control method.

DETAILED DESCRIPTION OF THE EXAMPLE EMBODIMENTS

Figure 1:
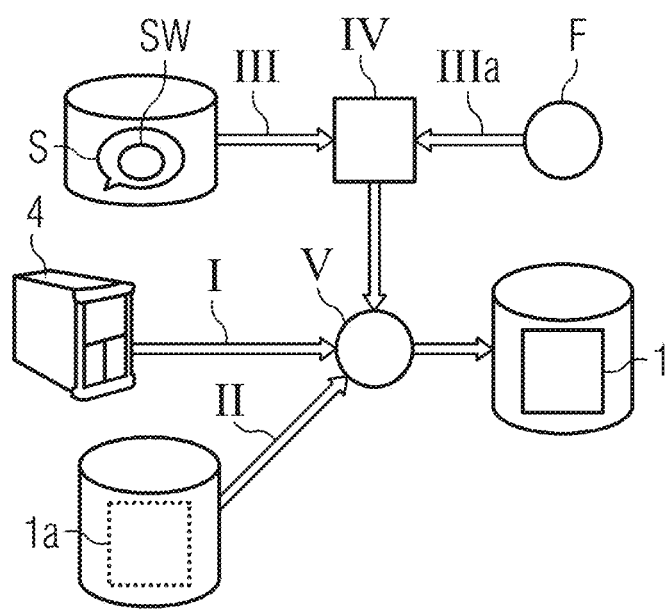
FIG. 1 shows a flow diagram for a possible workflow of an embodiment of an inventive method.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules.

Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the present invention is directed to a method serves to create ("train") a control unit (controller) that is suitable in particular for controlling an output unit from information in the context of medical diagnostics and therapy. The method comprises:

Providing a Learning Processing Apparatus

A learning processing apparatus is provided. This learning processing apparatus is designed via an algorithm to recognize spoken words. This means that spoken words are converted into "computer-intelligible" data objects. Recognition and conversion of speech in this way is known to a person skilled in the art.

Providing an Untrained Control Unit

An untrained control unit is provided on, or in, the learning processing apparatus. This untrained control unit is designed to be trained via machine learning. In this context, "untrained" means that the control unit may be fully untrained or may not be optimally trained. The control unit may comprise a trainable algorithm or an item of trainable hardware, e.g. a field-programmable gate array (FPGA).

Providing Speech Recordings

A number of speech recordings are provided. These speech recordings comprise the communication during a medical procedure. A diagnostic procedure, an operation or a therapeutic procedure represents such a medical procedure, for example. For example, the audio from a series of cardiac operations was recorded and these recordings are made available as speech recordings. The speech recordings may be made available through a RIS (radiology information system) or a PACS (picture archiving and communication system), for example.

The speech recordings concern comparable medical procedures. This means that the speech recordings concern, for example, cardiac operations or, for example, diagnostic procedures for comparable disease patterns. This comparability is an important point because the communication differs within different workflows. For example, wholly different words, commands and responses are used during a liver transplant than during an operation on the heart. An examination of the brain proceeds differently to an examination of the organs of movement. In summary, comparability can be the to exist preferably if the same medical procedure (e.g. operation, examination, imaging procedure, etc.) is being performed on the same area of the body.

Speech Analysis

A speech analysis of the speech recordings is now carried out. In particular, this speech analysis is carried out on a procedure-specific basis, where a procedure-specific meaning or use of terms is assumed and applied. The speech analysis is preferably performed directly by the learning processing apparatus.

Training

The control unit is trained according to a machine learning principle on the basis of the speech analysis of the speech recordings.

The inventive control unit of at least one embodiment is for controlling an output unit from information in the context of medical diagnostics and therapy is produced using the inventive method. It is a trained control unit that has been trained using embodiments of the inventive method.

The inventive control method of at least one embodiment serves to control in particular an output unit from information in the context of medical diagnostics and therapy. In particular, the control method serves to provide procedure-specific speech capture and analysis in medical diagnostics and therapy in an examination room. It should be noted that statements relating to special characteristics of components of the method described above preferably also apply to the corresponding components of the control method and vice versa. The control method of at least one embodiment includes:

Providing an inventive (trained) control unit or training a control unit in accordance with a method according to the invention.

Creating a speech recording during a medical procedure. In one simple case, this can involve the audio from a medical procedure being recorded (e.g. using microphones) during the workflow in an examination room. As a matter of course, the control unit must then have been trained on this procedure. A control unit that has been trained with speech recordings of a hip operation, for example, cannot be used effectively in a cardiac operation.

Processing the speech recording via the control unit while continuing to create the speech recording. This means that the control method is applied during the medical procedure. One part of the communication during the procedure is recorded, processed, and then the next part is recorded and processed.

In this context the control unit determines keywords in the speech recording and generates result output data based on the keywords. Individual keywords or keyword sequences (or combinations of keywords) may be used here. Essentially this principle was preferably also used during the training of the control unit. Here, the determination of keywords was performed by the learning processing apparatus, and the control unit trained to recognize these keywords. Nevertheless, the learning processing apparatus determined the result that followed these keywords and, during the training of the control unit, this result is linked to the respective keyword in the form of result output data.

Controlling the output unit with the result output data.

In this step, the result is preferably output acoustically via speech output, or optically e.g. through text, images or videos. The output may be provided on screens or through loudspeakers as the output unit. The output unit may then be controlled directly (e.g. a loudspeaker in an operating room) or also controlled via the internet.

An inventive information system of at least one embodiment for the output of information in the context of medical diagnostics and therapy comprises an inventive control unit of at least one embodiment, an output unit and a speech recording system, wherein the information system is designed to execute at least one embodiment of the inventive control method.

An inventive learning processing apparatus of at least one embodiment comprises a processor and a data storage device containing instructions which, on being executed, allow the processor to:

capture speech recordings provided to the learning processing apparatus, perform an analysis of the speech recordings (in particular, to recognize spoken words in the speech recordings as objects), if applicable, identify keywords from the words recognized and train a control unit according to at least one embodiment of an inventive method based on the analysis of the speech recordings.

A majority of the aforementioned components of the information system or control unit may be realized entirely or partially in the form of software modules in a processor of a corresponding information system. A realization largely through software has the advantage that conventionally used apparatuses can also easily be upgraded with a software update in order to operate in the manner according to of at least one embodiment the invention.

In this respect, at least one embodiment is also achieved by a corresponding computer program product comprising a computer program, which can be loaded directly into a computing system or a memory device of an information system and which contains program segments, in order to perform all the steps of the method according to of at least one embodiment the invention when the program is executed in the computing system or the information system. Such a computer program product can comprise, where relevant, in addition to the computer program, further components, such as, for example, documentation and/or additional components including hardware components, for example, hardware keys (dongles, etc.) in order to use the software.

For transfer to the computing system or to the information system, and/or for storage on, or in, the computing system or the information system, a computer-readable medium, for instance a memory stick, a hard disk or any other portable or permanently installed data storage medium can be used, on which are stored the program segments of the computer program, which program segments can be downloaded and executed by a computing system or an information system. For this, the processing unit can have, for example, one or more cooperating microprocessors or the like.

Therefore also preferred is an information system in the form of a computer program product comprising a computer program which can be loaded directly into a memory device of the information system and which contains program segments in order to perform all the steps of the identification method according to of at least one embodiment the invention when the computer program is executed in the information system.

An information system or an embodiment of the method or control method is preferred in the form of a computer-readable medium, on which are stored program segments which can be downloaded and executed by a processing unit in order to perform all the steps of a method or control method according to of at least one embodiment the invention when the program segments are executed by the processing unit. The identification unit in the form of this computer-readable medium can also exist as hardware, for instance as a programmed FPGA or EPROM.

Further, particularly advantageous embodiments and developments of the invention are given in the dependent claims and in the following description, where the claims in one category of claims can also be developed in a similar way to the claims and passages of the description in another category of claims, and in particular individual features of different example embodiments or variants can also be combined to create new example embodiments or variants.

The method may also comprise elements of "cloud computing". In "cloud computing", an IT infrastructure, e.g. storage space or computing power and/or application software is made available through a network. Communication between the user and the "cloud" then takes place via data interfaces and/or data transmission protocols.

In the context of "cloud computing", in one preferred embodiment of the inventive method, data is provided via a data channel (e.g. a network) to a "cloud". This "cloud" comprises a (remote) computing system, e.g. a computer cluster, which generally does not include the user's local computer. In particular, this cloud may be made available by the medical facility that also provides the medical systems. In particular, the imaging data is sent via a RIS or PACS to a (remote) computer system (the "cloud"). In data computational terms, the computing system of the "cloud", the network, and the medical system (in particular the information system described above) preferably form a composite system. The method can then be realized via a combination of commands in the network. The data or results calculated in the cloud are preferably sent back to the user's local computer via a data channel (e.g. via a network). For example, the image data provided is processed in accordance with the inventive method by a computer system of a hospital and the results of this processing are sent back to the user via a RIS or PACS.

In the context of one preferred embodiment of the inventive apparatus, the components relevant for at least one embodiment of the invention are present in the "cloud". A preferred system also comprises, in addition to such an apparatus, a local processing unit that is connected to the apparatus via a data channel (e.g. a network designed in particular as a RIS or PACS). The local processing unit comprises at least one data receiving interface for receiving data. It is also preferable if the local computer also has a transmission interface for sending data to the apparatus.

In one particularly preferred example embodiment of the method, the speech analysis of the speech recordings systematically captures keywords in the speech recordings, in particular their repetitions and chronological sequences. Individual keywords or keyword sequences (or combinations of keywords) may be examined here.

The speech analysis is preferably performed for each actor. A separate speech analysis is carried out for each person and associated with that person's function. For example, there will be a speech analysis for the physician, a speech analysis for an assistant (e.g. a nurse or technician) and a speech analysis for the patient.

For a captured keyword or an action linked to this keyword, the control unit is preferably trained on the subsequent action (or a proactive support of a subsequent action). Here the subsequent action (or a proactive support of the subsequent action) preferably comprises an equipment adjustment, such as a mechanical positioning, in particular a fine adjustment, a display of a sequence of activities for the personnel or the patient, or a display of X-ray images (or X-ray image sequences).

The speech analysis of the speech recordings is preferably linked to an activity analysis and/or action analysis based on film images of the medical procedure. Here the timings of the keywords, i.e. the points in time at which the keywords were the, are preferably systematically computationally linked to actions by the actors on the system and/or in the room, taken from the film images. In this way, actions can be systematically correlated with keywords.

A comparative speech analysis of a multiplicity of identical procedures is preferably performed (e.g. a hip operation, a cardiac operation, a diagnostic procedure). This is then used as a way of optimizing the training of the control unit. A comparative speech analysis of the duration of the procedure, the frequency and number of keywords, the duration of speech communication and such like is preferably performed.

The speech recording is preferably created by capturing the communication in an examination room, preferably using a number of microphones. These are preferably ceiling-mounted microphones and/or microphones fixed to an item of equipment and/or integrated into a table.

The speech recording (i.e. the communication recorded in the examination room) is preferably analyzed in respect of the best means of capture by the different microphones, e.g. a table microphone is used for an operator located at the table instead of a ceiling microphone located in the room, because in this case the speech quality from the table microphone is better.

In addition, an optical recording of areas of the examination room is preferably also performed, preferably via a number of cameras. Particularly preferably, a number of 3D cameras can be used as the cameras.

Result output data is preferably generated automatically based on keywords linked to the optical capture (by camera monitoring). This is done in particular for dedicated control steps. For example, it is determined whether an operating instrument for a procedure is not present, or whether an operating instrument is missing compared with the start of the procedure.

For a captured keyword or an action linked to this keyword, a subsequent action (or a proactive support of a subsequent action) learned by the control unit is preferably contained in the result output data. Here the subsequent action (or a proactive support of the subsequent action) preferably comprises an equipment adjustment, such as a mechanical positioning, in particular a fine adjustment, a display of a sequence of activities for the personnel or the patient, or a display of X-ray images (or X-ray image sequences).

Preferably the control unit is preferably designed such that people can ask questions during the medical procedure (e.g. in an examination room) through microphones and the control unit generates, from keywords in the questions, (predetermined) answers as result output data. These answers can be linked to predetermined answers, for example, so that with the combination of keywords "information about the patient", result output data is output that controls the output unit such that it outputs the medical record.

The output unit preferably comprises loudspeakers in the examination room, e.g. integrated in a medical system, an item of medical equipment and/or in a table. Here the result output data output in this way is designed so as to produce a synthetic speech output through the loudspeakers. In this way, the loudspeakers can be used systematically for speech transmission or speech output. Here the control unit is preferably designed such that it generates the result output data in such a way that specific information is output to an actor in the examination room via a nearby loudspeaker.

The control unit is preferably designed such that help can be requested through it using voice control (via keywords). Here the control unit is preferably designed such that it outputs result output data comprising film data for documentation purposes. In this way, for example a "role model" film can be output; this is preferably kept as a film image stored in a storage area and can be accessed as required during the procedure. By way of example, the output of a previously performed action, e.g. an X-ray fluoroscopy scene or the film output of an earlier captured (OP) action, would also be a control function. When accessed, the film image is preferably automatically integrated into the result output data.

The result output data preferably comprises data for a synthetic speech output. With the aid of the communications captured for dedicated procedures, voice commands or spoken information are preferably systematically then played back during a medical procedure through the loudspeakers installed on the system or in the room, on the basis of actions or a chronological sequence of keywords. Here the control unit is preferably designed such that a synthetic speech output can be activated for dedicated actors (e.g. an MTA, operator). This activation can be performed automatically, manually or by keyword.

Preferably the output produced via the result output data (e.g. a synthetic speech output or a film playback) is systematically analyzed, in a further phase during and/or after it has been output, with regard to its acceptance by the actors. For example, the sequence of words "That was not helpful" will indicate that the output was not appropriate. This allows the efficiency of the control unit to be measured. Here the usefulness of the output is examined, and the control unit may be trained further as a result.

Advantages of embodiments of the invention reside in the fact that for the first time the connection between speech and an associated action by the actor can be established, communication can be captured and used as a means of workflow optimization, communication can furthermore be used to develop and optimize synthetic speech outputs, and synthetic speech outputs can be used for information and control purposes in procedures. Errors can be avoided as a result. Inefficient workflows and communications can also be captured and subsequently avoided.

FIG. 1 shows a flow diagram for a possible workflow of an embodiment of an inventive method to create a control unit 1 for controlling an output unit 2 (see e.g. FIG. 2) from information in the context of medical diagnostics and therapy. The method comprises the following steps:

In step I, a learning processing apparatus 4 is provided. This learning processing apparatus 4 is designed via an algorithm to recognize spoken words and as a matter of course also to train a control unit (controller, including at least one processor for example, in at least one embodiment) 1. The learning processing apparatus 4 can, as shown here, be a high-powered computer, but it can also be a virtual machine in a computing system.

In step II, an untrained control unit 1a is provided, which is designed to be trained via machine learning. This control unit 1a can be an untrained algorithm provided as software on the learning processing apparatus 4, but it can also be a hardware unit, e.g. a programmable field array (FPGA) or a dedicated small computer provided in the learning processing apparatus 4 (i.e. connected to the learning processing apparatus 4).

In step III, a number of speech recordings S are provided, which comprise the communication during a medical procedure. A speech recording is represented here by a speech bubble, which symbolizes information in a spoken communication and here comprises a keyword SW. A multiplicity of such speech recordings S is used in this method for the training, wherein all these speech recordings S concern comparable medical procedures, e.g. a hip operation or an X-ray recording of the abdominal cavity.

In step IV, a speech analysis of the speech recordings S is performed. The speech analysis is preferably performed directly by the learning processing apparatus 4.

In the speech analysis of the speech recordings S, keywords SW in the speech recordings S are preferably systematically captured, e.g. repetitions and chronological sequences of the keywords SW.

It is advantageous for the speech analysis of the speech recordings S to be linked to an activity analysis or action analysis based on film images F of the medical procedure. Here the timings of the keywords SW, i.e. the points in time at which the keywords were the, are preferably systematically computationally linked to actions by the actors on the system and/or in the room, taken from the film images F.

These film images F are provided in the optional step IIIa.

In step V, represented here by a circle, training of the untrained control unit 1a is performed according to a machine learning principle on the basis of the speech analysis of the speech recordings S. This training is performed on the learning processing apparatus, which is symbolically brought into the circle with the arrow to step I.

A trained control unit 1 is obtained as a result.

Figure 2:
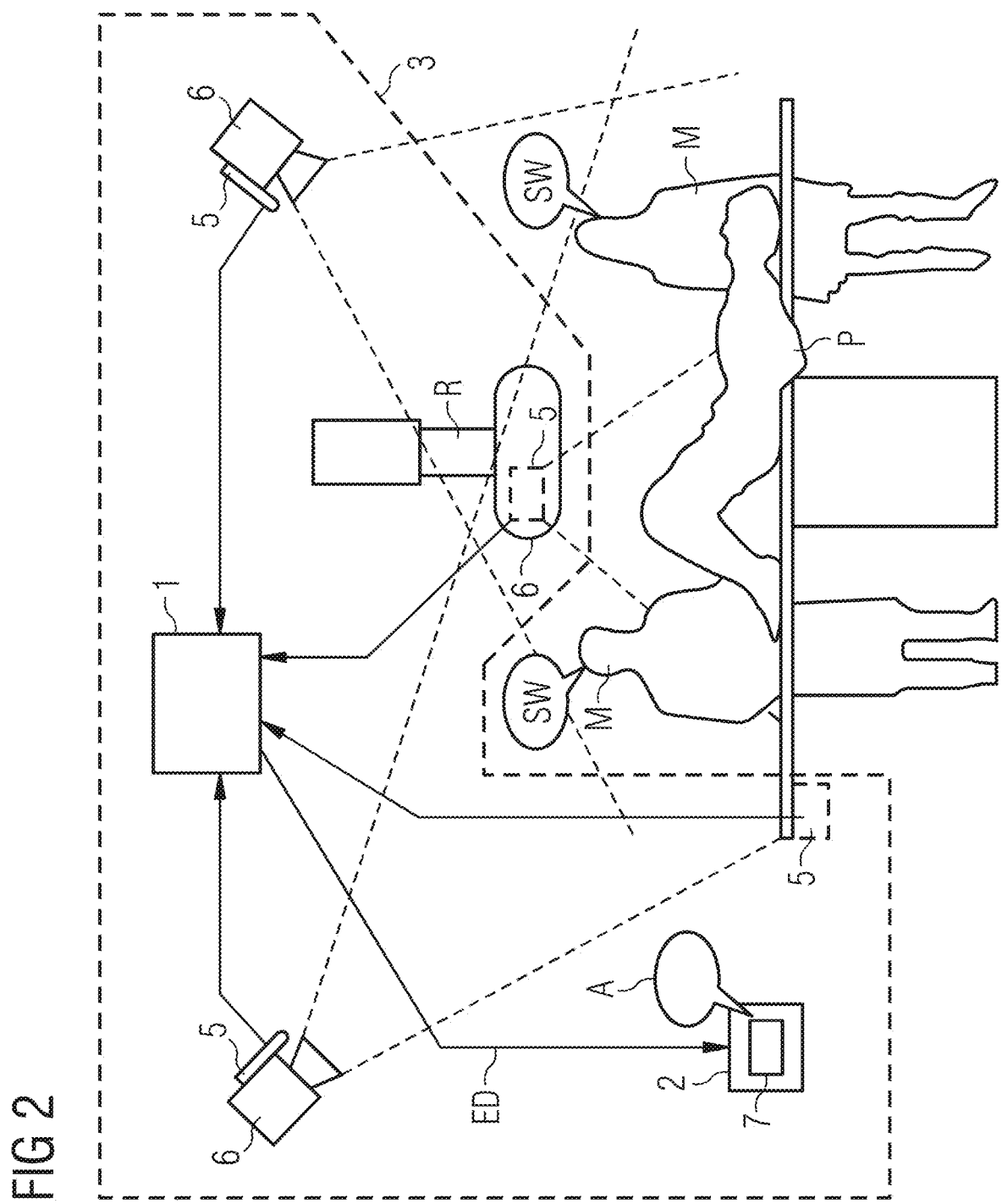
FIG. 2 shows a highly schematic representation of a preferred information system.

FIG. 2 shows a highly schematic representation of a preferred information system 3. In the following explanations it is assumed that the scene represented is an X-ray examination. In principle, however, the method can be used advantageously for a multiplicity of different medical workflows, such as e.g. operations or examinations.

In an examination room a patient P is lying beneath an X-ray device R on a couch and awaiting an imaging procedure on the lower abdomen. Two medical professionals M are standing to the side of the patient P and discussing the workflow for the imaging procedure. Located on the ceiling of the examination room are two cameras 6, which monitor the examination room and create film images F. These cameras have microphones 5, which record the discussion taking place in the examination room as speech recordings S. In addition, another camera 6 together with a microphone 5 is located in the X-ray device. Here, the camera 6 records the patient and any responses he or she makes. A further microphone is located on the couch.

The speech recordings are captured by the control unit 1 and evaluated with a speech analysis, or rather only the one with the best speech quality. In addition, in this example the film images F created with the cameras 6 are evaluated or analyzed as well. Result output data ED is generated by the trained control unit 1 in response to the keywords SW of the medical professionals M recognized in the speech analysis and a (speech) output A is output via this result output data ED through a loudspeaker 7.

For example, the person M standing to the right could ask the person M standing to the left what X-ray energy needs to be set for the patient P. The person M standing to the left says "Medical record please". The control unit then recognizes the keyword "medical record" from the person M standing to the left and the keyword sequence "what X-ray energy" from the person M standing to the right, and then searches for a corresponding entry in the medical record, and generates result output data ED with a sound file, which is output through the loudspeaker 7. The output A could be "Patient P was previously irradiated with X keV of energy".

FIG. 3 shows a flow diagram for a possible workflow of an embodiment of an inventive control method for controlling an output unit 2 from information in the context of medical diagnostics and therapy.

In step VI, a trained control unit 1 is provided (see e.g. FIG. 1).

In step VII, a speech recording S is created during a medical procedure.

In step VIII, the speech recording S is processed via the control unit 1. The control unit 1 determines keywords SW in the respectively created speech recording S and generates result output data ED based on these keywords SW.

The arrow leading back to step VII indicates that these two steps are continuously repeated such that the creation of the speech recording S proceeds continuously.

In step IX, the output unit 2 is controlled with the result output data ED.

Finally it should be reiterated that the embodiments described in detail above are merely example embodiments, which can be modified by a person skilled in the art in many ways without departing from the scope of the invention. In addition, the use of the indefinite article "a" or "an" does not rule out the possibility of there also being more than one of the features concerned. Likewise, the terms "unit" and "module" do not exclude the possibility that the components in question include of a plurality of interacting sub-components, which may also be spatially distributed if applicable.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for creating a controller for controlling an output device from information in a context of medical diagnostics and therapy, the method comprising:
    recognizing, via a learning processing apparatus, spoken words spoken by a plurality of actors, the learning processing apparatus including an algorithm for recognizing spoken words; and
    training an untrained controller, via machine learning, to predict a subsequent action performed by the plurality of actors following a captured keyword by
        providing a number of speech recordings, each speech recording of the number of speech recordings including a communication during a medical procedure, wherein the number of speech recordings concern comparable medical procedures,
        performing a speech analysis of the speech recordings, and
        training the untrained controller according to a machine learning principle based upon the speech analysis of the speech recordings,
        wherein the untrained controller is on, or in, the learning processing apparatus.

2. The method of claim 1,
    wherein the performing the speech analysis includes capturing keywords in the speech recordings,
    wherein the training the untrained controller includes, for the captured keyword or an action linked to the captured keyword, training the controller on the subsequent action, the subsequent action including at least one of an equipment adjustment, a display of a sequence of activities for personnel or a patient, or a display of X-ray images.

3. The method of claim 2, further comprising at least one of:
    analyzing the speech recordings systematically to capture repetitions and chronological sequences; or
    performing the speech analysis for each actor.

4. The method of claim 1, wherein the training the untrained controller includes
    linking the speech analysis of the speech recordings to at least one of an activity analysis or an action analysis based on film images of the medical procedure, and
    computationally linking timings of keywords to actions by actors performed at least one of on a system or in a room, the actions taken from the film images.

5. The method of claim 1, further comprising:
    performing a comparative speech analysis of a multiplicity of identical procedures,
    wherein the training the controller includes optimizing the controller based on the comparative speech analysis.

6. The method of claim 5, wherein the training the controller includes optimizing the controller with regard to duration of the procedure, a frequency and number of keywords, and a duration of speech communication.

7. A non-transitory computer-readable medium, storing program segments downloadable and executable by a processor, to perform the method of claim 1, when the program segments are executed by the processor.

8. A controller for controlling an output device from information in a context of medical diagnostics and therapy, the controller comprising:
    circuitry configured to cause the controller to
        recognize, via an algorithm for recognizing spoken words, spoken words spoken by a plurality of actors; and
        train an untrained controller, via machine learning, to predict a subsequent action performed by the plurality of actors following a captured keyword by
            providing a number of speech recordings, each speech recording of the number of speech recordings including a communication during a medical procedure, wherein the number of speech recordings concern comparable medical procedures,
            performing a speech analysis of the speech recordings, and
            training the untrained controller according to a machine learning principle based upon the speech analysis of the speech recordings.

9. The controller of claim 8, wherein the circuitry is further configured to cause the controller to,
    create a speech recording during a medical procedure;
    process the speech recording while continuing to create the speech recording;
    determine the captured keywords in the speech recording;
    generate result output data based on the captured keywords; and
    control the output device with the result output data.

10. The controller of claim 9, wherein circuitry is further configured to cause the controller to:
    create the speech recording from the communication in an examination room captured using a plurality of microphones;
    analyze the speech recording to determine a best way to capture by different microphones of the plurality of microphones; and
    generate result output data based on at least one of keywords linked to an optical capture for the captured keyword, or an action linked to the captured keyword, the optical capture being an optical recording of areas of the examination room performed via number of cameras, the result output data including the subsequent action learned by the controller,
    wherein the subsequent action includes at least one of an equipment adjustment, a display of a sequence of activities for personnel or a patient, or a display of X-ray images.

11. The controller of claim 10, wherein the circuitry is further configured to cause the controller to:

generate, from keywords included in questions asked during the medical procedure through the microphones, answers as the result output data.

12. The controller of claim 11, wherein the circuitry is further configured to cause the controller to:
   generate the output data to produce a synthetic speech; and
   output the synthetic speech through a proximate loudspeaker, of a plurality of loudspeakers included in the output device, such that specific information is output to an actor in the examination room via the proximate loudspeaker.

13. The controller of claim 10, wherein the circuitry is further configured to cause the controller to:
   generate the output data to produce a synthetic speech; and
   output the synthetic speech through a proximate loudspeaker, of a plurality of loudspeakers included in the output device, such that specific information is output to an actor in the examination room via the proximate loudspeaker.

14. The controller of claim 9, wherein the circuitry is further configured to cause the controller to:
   generate the output data to produce a synthetic speech; and
   output the synthetic speech through a proximate loudspeaker, of a plurality of loudspeakers included in the output device, such that specific information is output to an actor in an examination room via the proximate loudspeaker.

15. The controller of claim 9, wherein the circuitry is further configured to cause the controller to,
   output result output data including film data for documentation purposes in response to a request for help, the request for help requested via voice control.

16. The controller of claim 9, wherein the result output data includes data for an output, and the circuitry is further configured to cause the controller to activate an output for dedicated actors.

17. The controller of claim 9, wherein circuitry is further configured to cause the controller to systematically analyze the output produced via the result output data at least one of during or after output, with regard to acceptance by actors.

18. An information system for the output of information in the context of medical diagnostics and therapy, comprising:
   the controller of claim 8;
   an output device; and
   a speech recording
   wherein the circuitry is further configured to cause the information system to
      process the speech recording while continuing to create the speech recording,
      determine the captured keywords in the speech recording,
      generate result output data based on the captured keywords, and
      control the output device with the result output data.

19. A non-transitory computer program product, storing a computer program, directly loadable into a memory device of a computing system or an information system, for output of information in a context of medical diagnostics and therapy, the computer program including program segments, to perform a control method, when the computer program is executed in the computing system or the information system, the control method comprising:
   recognizing, via an algorithm for recognizing spoken words, spoken words spoken by a plurality of actors;
   training an untrained controller, via machine learning, to predict a subsequent action performed by the plurality of actors following a captured keyword by
      providing a number of speech recordings, each speech recording of the number of speech recordings including a communication during a medical procedure, wherein the number of speech recordings concern comparable medical procedures,
      performing a speech analysis of the speech recordings, and
      training the untrained controller according to a machine learning principle based upon the speech analysis of the speech recordings;
   creating a speech recording during a medical procedure;
   processing the speech recording while continuing to create the speech recording;
   determining the captured keywords in the speech recording;
   generating result output data based on the captured keywords; and
   controlling an output device with the result output data.

* * * * *